US006937689B2

(12) United States Patent
Zhao et al.

(10) Patent No.: US 6,937,689 B2
(45) Date of Patent: Aug. 30, 2005

(54) METHODS AND APPARATUS FOR IMAGE RECONSTRUCTION IN DISTRIBUTED X-RAY SOURCE CT SYSTEMS

(75) Inventors: Qi Zhao, Ossining, NY (US); Peter Michael Edic, Albany, NY (US); Bruno Kristiaan Bernard De Man, Clifton Park, NY (US); Samit Kumar Basu, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 102 days.

(21) Appl. No.: 10/704,179

(22) Filed: Nov. 7, 2003

(65) Prior Publication Data

US 2005/0100127 A1 May 12, 2005

(51) Int. Cl.[7] .................................................. A61B 6/03
(52) U.S. Cl. ........................................... 378/9; 378/901
(58) Field of Search ............................. 378/1, 8, 9, 15, 378/901

(56) References Cited

U.S. PATENT DOCUMENTS 4,463,375 A * 7/1984 Macovski ................. 378/98.12

OTHER PUBLICATIONS

Nitin Aggarwal, Marios S. Pattichis, Jackie Shen, Richard Leahy, James Theiler, Andrew Fraser and Guillermal Sapiro, "*Image Analysis and Understanding Data from Scientific Experiments*," Los Alamos National Laboratory Workshop, Dec. 2–6, 2002.

Yoram Bresler, "*Unified Time–Sequential Sampling Theory for Spatio–Temporal Signals*," Department of Mathematics, University of Illinois at Urbana–Champaign, Nov. 19, 1998.

Yoram Bresler and N. Parker Willis, "*Optical Scan Design for Time–Varying Tomographic Imaging*," IEEE, 1993.

N. Parker Willis and Yoram Bresler, "*A New Approach to the Time–Sequential Sampling Problem*," IEEE, 1992.

N. Parker Willis and Yoram Bresler, "*Optimal Scan Design for Tomographic Imaging of Time Varying Distributions*," IEEE, 1991.

N. Parker Willis and Yoram Bresler, "*New Results on Time–Sequential Sampling*," Department of Electrical Engineering, University of Illinois at Urbana–Champaign, Date Unknown.

Nitin Aggarwal, "*Dynamic Cardiac MR Imaging Based on Time–Sequential Sampling Theory*," DSP Seminar, Nov. 6, Year Unknown.

* cited by examiner

*Primary Examiner*—David V Bruce
(74) *Attorney, Agent, or Firm*—Fletcher Yoder

(57) ABSTRACT

A method for imaging an object that includes utilizing a computed tomography imaging apparatus having a distributed x-ray source to acquire samples of projection data of an object in angular and temporal space utilizing a predetermined sampling lattice. Acquired projection data is filtered utilizing a two-dimensional linear filter to produce filtered data, and the filtered data is then backprojected to obtain a reconstructed image of the object.

20 Claims, 7 Drawing Sheets

METHODS AND APPARATUS FOR IMAGE RECONSTRUCTION IN DISTRIBUTED X-RAY SOURCE CT SYSTEMS

BACKGROUND OF THE INVENTION

This invention relates generally to computed tomography (CT) imaging systems and more particularly to methods and apparatus for increased quality imaging, especially of moving objects, in distributed x-ray source CT imaging systems.

In computed tomography (CT) imaging systems employing rotating gantries, fan beam projections are collected linearly (progressively) at a regular sampling interval in an angular direction. For cardiac imaging, heart motion produces motion artifacts, the severity of which depend upon the speed of a rotating gantry incorporating an x-ray source and detector array. Projection data must be collected rapidly to avoid these motion artifacts. This requirement on the collection of projection data imposes technically challenging requirements on the speed at which the gantry must be able to rotate and on the flux output of the x-ray tube used as the x-ray source.

In at least one known rotating gantry CT imaging system, projection data for the same cardiac phase acquired during multiple heart cycles is used to reduce motion artifacts. An electrocardiogram (EKG) signal is acquired concurrently during a scan, or a pseudo-EKG signal is generated using the projection data itself to aid in retrospective identification of projection data acquired at a particular phase of the cardiac cycle. Because heart motion is assumed to be regular and periodic in this artifact reduction method, any irregularity or aperiodicity of heart motion will result in a degradation in image quality.

Another known CT imaging system utilizes an electrically steered electron beam to generate a moving x-ray beam. This imaging system can effectively suppress motion artifacts, but the motion-suppressed images have a relatively low signal-to-noise ratio.

BRIEF DESCRIPTION OF THE INVENTION

Some configurations of the present invention therefore provide a method for imaging an object that includes utilizing a computed tomography imaging apparatus having a distributed x-ray source to acquire samples of projection data of an object in angular and temporal space utilizing a predetermined sampling lattice. Acquired projections are filtered utilizing a two-dimensional linear filter to produce filtered data, and the filtered data is then backprojected to obtain a reconstructed image of the object.

Also, some configurations of the present invention provide a method for imaging an object that includes utilizing a computed tomography imaging apparatus having a distributed x-ray source to acquire samples of projection data of an object in angular and temporal space utilizing a predetermined sampling lattice. The predetermined sampling lattice is a sampling lattice chosen to be time-sequential with respect to spatial support S defined as a sampling range of view angles θ and at least tightly packs the spectral support B of the object in the frequency domain of the sampled signal. The method further includes filtering acquired projection data utilizing a two-dimensional linear filter having a constant frequency response inside a predefined spectral support and zero frequency response elsewhere; and backprojecting the filtered data to obtain a reconstructed image of the object.

Still other configurations of the present invention provide a computed tomography imaging apparatus that includes a distributed x-ray source and a detector configured to acquire samples of projection data of an object in angular and temporal space utilizing a predetermined sampling lattice. The apparatus is configured to filter acquired projection data utilizing a two-dimensional linear filter to produce filtered data and then backproject the filtered data to obtain a reconstructed image of the object.

Yet other configurations of the present invention provide a computed tomography imaging apparatus that includes a distributed x-ray source and a detector configured to acquire samples of projection data of an object in angular and temporal space utilizing a predetermined sampling lattice. The predetermined sampling lattice is a sampling lattice that is chosen to be time-sequential with respect to spatial support S defined as a sampling range of view angles θ and that at least tightly packs spectral support B of the projection data in the frequency domain of the sampled signal. The apparatus is configured to filter acquired projection data utilizing a two-dimensional linear filter having a constant frequency response inside a predefined spectral support and zero frequency response elsewhere to produce filtered data, and to backproject the filtered data to obtain a reconstructed image of the object.

Methods and apparatus of the present invention will thus be seen to suppress motion artifacts effectively while maintaining a high signal-to-noise ratio in reconstructed images of a moving object. Moreover, it will be appreciated that methods and apparatus of the present invention are particularly useful for cardiac CT imaging, inasmuch as the suppression of motion artifacts does not depend upon the periodicity and regularity of the motion of the heart.

DETAILED DESCRIPTION OF THE INVENTION

Figure 1:
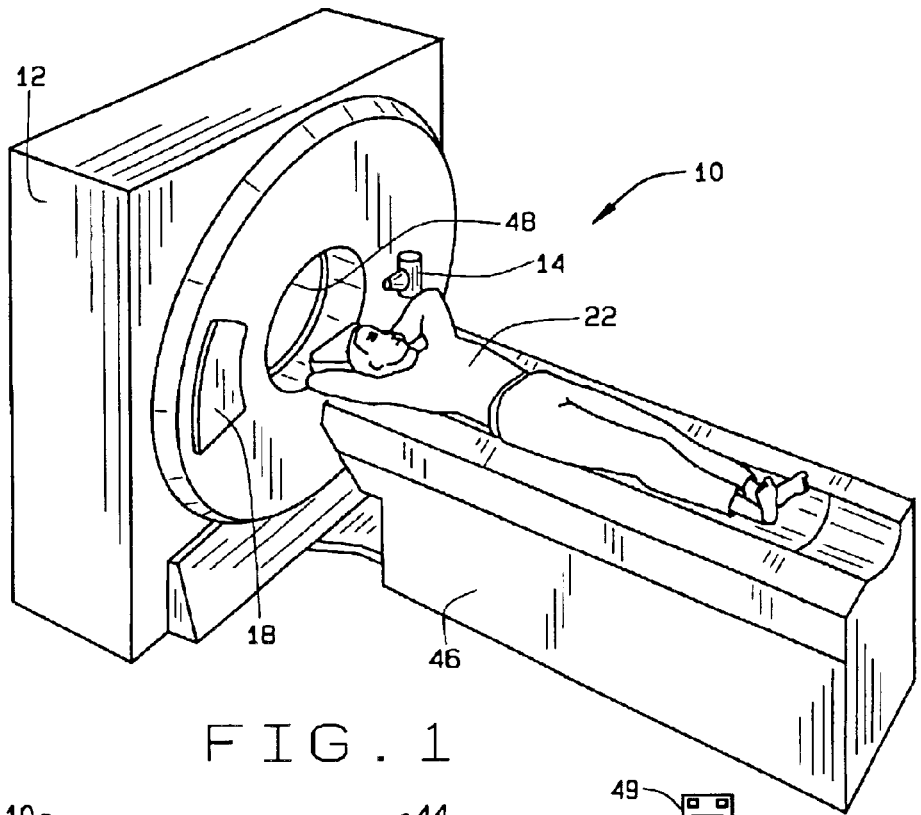
FIG. 1 is a pictorial view representative of configurations of a CT imaging apparatus of the present invention.

Example configurations of methods and apparatus that facilitate reconstruction of images in computed tomographic (CT) imaging systems are described below in detail. A technical effect of the methods and apparatus described herein include at least one of the facilitating of the imaging of a moving object or reduction in motion artifacts in an image of the object, irrespective of whether the object moves periodically or irregularly.

In some known CT imaging system configurations, an x-ray source projects a fan-shaped beam which is collimated to lie within an X-Y plane of a Cartesian coordinate system and generally referred to as an "imaging plane". The x-ray beam passes through an object being imaged, such as a patient. The beam, after being attenuated by the object, impinges upon an array of radiation detectors. The intensity of the attenuated radiation beam received at the detector array is dependent upon the attenuation of an x-ray beam by the object. Each detector element of the array produces a separate electrical signal that is a measurement of the beam intensity at the detector location. The intensity measurements from all the detectors are acquired separately to produce a transmission profile.

A group of processed x-ray attenuation measurements, i.e., projection data, from the detector array at one gantry angle is referred to as a "view". A "scan" of the object comprises a set of views made at different gantry angles, or view angles, during one revolution of the x-ray source and detector about the object being imaged.

In an axial scan, the projection data is processed to construct an image that corresponds to a two-dimensional slice taken through the object. One method for reconstructing an image from a set of projection data is referred to in the art as the filtered backprojection technique. This process converts the attenuation measurements from a scan into integers called "CT numbers" or "Hounsfield units" (HU), which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix of projection data acquired from the object. The helix mapped out by the fan beam yields projection data from which images in each prescribed slice may be reconstructed.

Reconstruction algorithms for helical scanning typically use helical weighing algorithms that weight the collected data as a function of view angle and detector channel index. Specifically, prior to a filtered backprojection process, the data is weighted according to a helical weighing factor, which is a function of both the gantry angle and detector angle. The weighted data is then processed to generate CT numbers and to construct an image that corresponds to a two-dimensional slice taken through the object.

To further reduce the total acquisition time, multi-slice CT systems have been introduced. In multi-slice CT, multiple rows of projection data are acquired simultaneously at any time instant. When combined with the helical scan mode, the system generates a single helix of multi-slice projection data. Similar to the single slice helical, weighting scheme, a method can be derived to multiply the weight with the projection data prior to applying the filtered backprojection algorithm.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. However, many embodiments generate (or are configured to generate) at least one viewable image.

Figure 2:
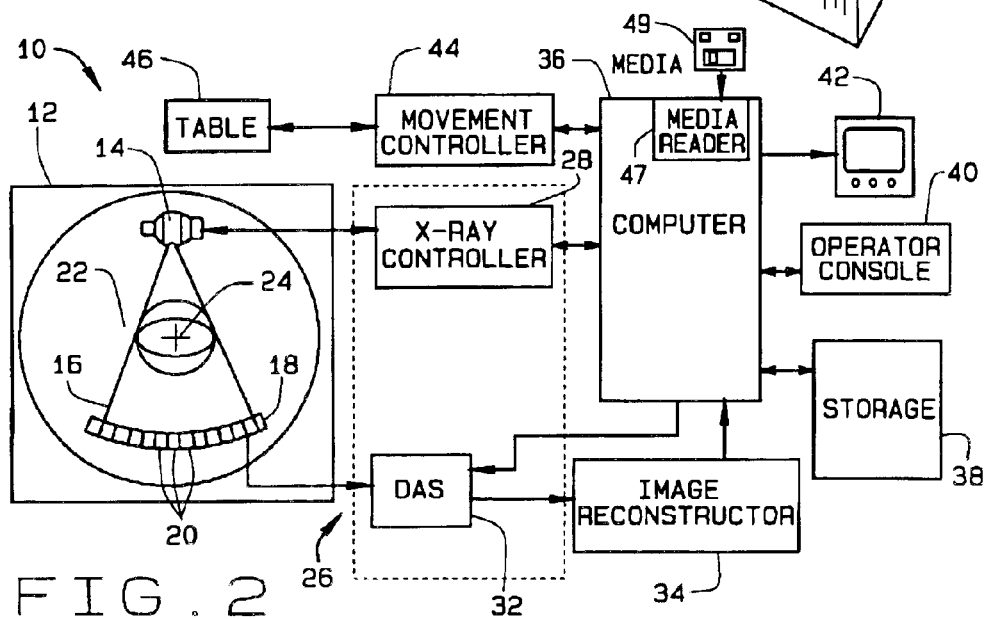
FIG. 2 is a block schematic diagram of the apparatus illustrated in FIG. 1.

Referring to FIG. 1 and FIG. 2, a computed tomography (CT) imaging system 10 is shown as including a gantry 12. Gantry 12 has at least one x-ray source or tube 14 that projects a beam of x-rays 16 toward a detector array 18 on the opposite side of gantry 12.

Detector array 18 comprises a plurality of detection elements 20 that together sense the projected x-rays that pass through an object, such as a medical patient 22 between array 18 and source 14. Each detection element 20 produces an electrical signal that represents the intensity of an impinging x-ray beam and hence can be used to estimate the attenuation of the beam as it passes through object or patient 22. FIG. 2 shows only a single row of detection elements 20 (i.e., a detector row). However, a multi-slice detector array 18 includes a plurality of parallel rows of detection elements 20 such that projection data corresponding to a plurality of quasi-parallel or parallel slices can be acquired simultaneously during a scan, or an area detector can be utilized to acquired cone-beam data. Moreover, the detector elements 20 may completely encircle the patient 22. FIG. 2 also shows a single x-ray source 14; however, many such x-ray sources are positioned around gantry 12.

Operation of x-ray source 14 is governed by a control mechanism 26 of CT system 10. Control mechanism 26 includes an x-ray controller 28 that provides power and timing signals to one or more x-ray sources 14. A data acquisition system (DAS) 32 in control mechanism 26 samples analog data from detection elements 20 and converts the data to digital signals for subsequent processing. An image reconstructor 34 receives sampled and digitized x-ray data from DAS 32 and performs high-speed image reconstruction. The reconstructed image is applied as an input to a computer 36, which stores the image in a mass storage device 38. The image reconstructor 34 may be specialized hardware residing in computer 36 or software executed by computer 36.

Computer 36 also receives signals via a user interface or graphical user interface (GUI). Specifically, computer 36 receives commands and scanning parameters from an operator console 40 that in some configurations includes a keyboard and mouse (not shown). An associated display 42 (for example, a cathode ray tube display) allows the operator to observe the reconstructed image and other data from computer 36. The operator supplied commands and parameters are used by computer 36 to provide control signals and information to x-ray controller 28, DAS 32, and a table motor controller 44 in communication with a table 46, which controls a motorized table 46 to position patient 22 in gantry 12. Particularly, table 46 moves portions of patient 22 through gantry opening 48.

In some configurations, computer 36 includes a device 47, for example, a floppy disk drive, CD-ROM drive, DVD drive, magnetic optical disk (MOD) device, or any other digital device including a network connecting device such as an Ethernet device for reading instructions and/or data from a computer-readable medium, such as a floppy disk 49, a CD-ROM, a DVD or another digital source such as a network or the Internet, as well as yet to be developed digital means. In other configurations, computer 36 executes instructions stored in firmware (not shown). Computer 36 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein. Although the specific configurations described herein refer to CT imaging systems having a stationary detector and x-ray source (or more precisely, a plurality of stationary x-ray sources each capable of projecting a directed x-ray beam, not necessarily all at once) it is contemplated that the benefits of the invention described herein accrue to imaging modalities other than CT. Additional, although the herein described methods and apparatus are described in a medical setting, it is contemplated that the benefits of the invention accrue to non-medical imaging systems such as those systems typically employed in an industrial setting or a transportation setting, such as, for example, but not limited to, a baggage scanning system for an airport or other transportation center.

Figure 3:
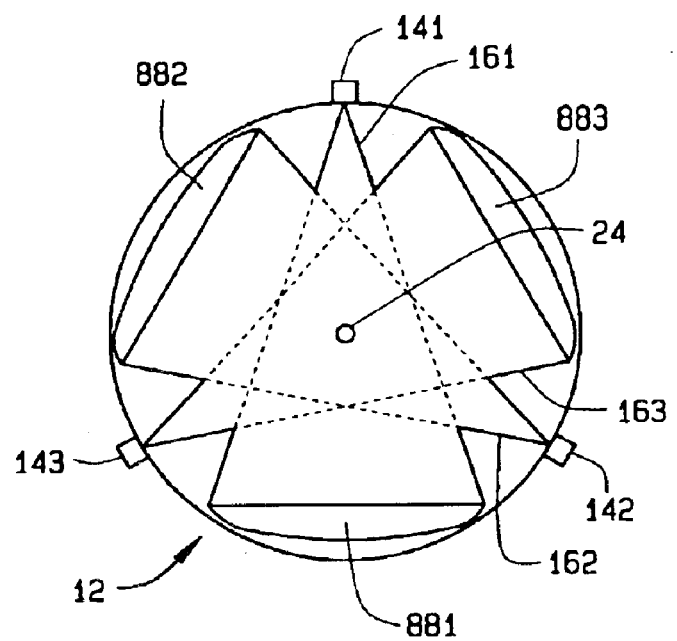
FIG. 3 is a diagrammatic view of a scan utilizing multiple x-ray tubes and detectors as in some configurations of the present invention.

Referring now to FIG. 3 an interior view of a gantry 12 of a computed tomography (CT) imaging system that does not require a rotating x-ray source is illustrated. One such system utilizing multiple x-ray sources is disclosed, for example, in U.S. Pat. No. 6,385,292 B1, issued May 7, 2002. (Other multisource type x-ray CT apparatus are disclosed in U.S. patent application Ser. No. US 2003/0072407 A1, published Apr. 17, 2003, and U.S. Pat. No. 4,592,079, issued May 27, 1986). A continuously formed tube could also be used.

In FIG. 3, a first, second and third x-ray source 141, 142, and 143 are used to generate respective x-rays 161, 162, and 163. These sources are representative of many such sources surrounding gantry 12. Each of x-rays 161, 162, and 163 impinge upon a corresponding detector segment 881, 882, and 883 of detector 18 shown in FIG. 1 and FIG. 2. By using a device without a rotating gantry, each of the x-ray sources, x-rays, and detectors are fixed relative to one another. A few representative examples are shown as x-ray sources 141, 142, and 143, x-rays 161, 162, and 163, and detectors 881, 882, and 883. One or multiple sources may be activated during a certain scanning interval.

Such systems can be substantially faster in the generation of an image than systems using a rotating gantry. Faster scan times are achievable because the location of the source of the x-ray beam used for scanning can be electronically switched, thereby making fast cardiac imaging possible. Power levels can be reduced relative to rotating gantry configurations because imaging system configurations of the present invention can be positioned closer to the patient, thereby reducing the emitted x-ray intensities needed for imaging.

To improve temporal resolution of a CT imaging apparatus 10 having multiple or distributed x-ray sources, an optimal time-sequential sampling pattern is provided. Projections are collected in a range from 0 to 360 degrees, subject to a time-sequential constraint that there is only one projection acquired at any time instant. Thus, the sampling is considered time-sequential. The sampling pattern specifies the angular position of which projection data set, i.e. the angular orientation of the view, to collect at any given time. It is optimal in the sense that it maximizes the temporal inter-projection interval, while providing a method for eliminating motion artifacts. This method can also be extended to configurations in which multiple sources are turned on simultaneously. In configurations in which it is impossible or impractical to achieve the optimal sampling pattern, some of the advantages of the present invention are achieved by configurations in which samples are collected in a pattern approximating an optimal sampling pattern.

Figure 4:
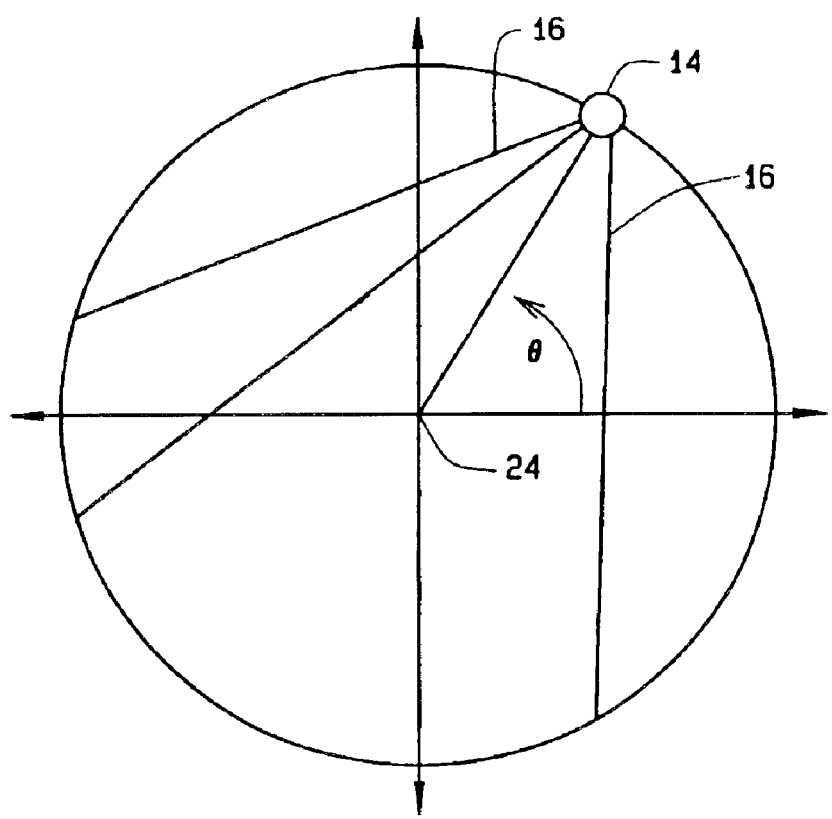
FIG. 4 is a representation of a fan-shaped beam emanating from an x-ray source in a computed tomography imaging apparatus, showing definitions of various angles used in the description of configurations of the present invention.

Referring to FIG. 4, a fan beam projection of the time varying object is denoted as $f(\rho,\theta,t)$, where $\rho$ (not shown in FIG. 4) is in a direction of the projection data profile while the source is at the $\theta$ orientation. Some configurations of the present invention reconstruct $f(\rho,\theta,t)$ using time-sequential samples while maximizing the temporal interval between two successive samples. Some configurations make use of assumptions regarding $f(\rho,\theta,t)$ for particular imaging uses. These assumptions concern, for example, spatial support of the object and/or the associated spectral support of the projection data acquired from the object.

Figure 5:
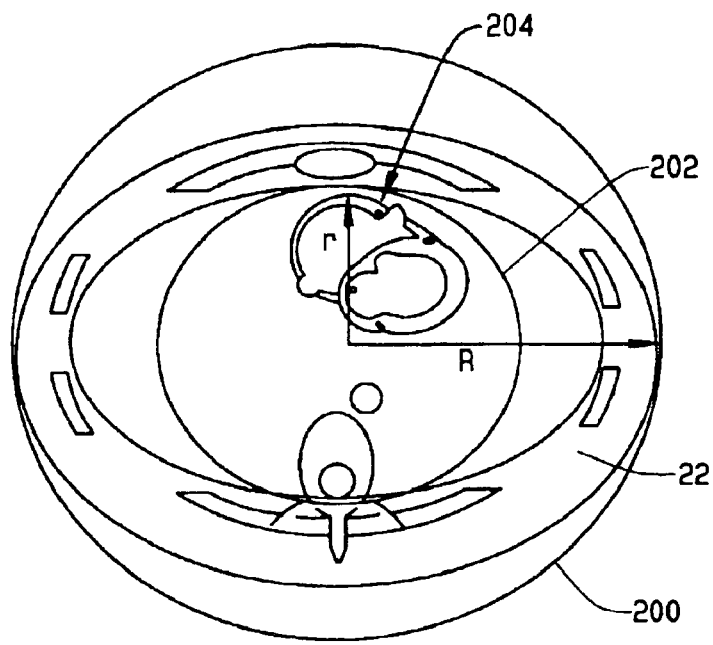
FIG. 5 is a representation of regions of interest of a patient being imaged.

For cardiac imaging, and referring to FIG. 5, two regions of interest (ROIs) are defined. As shown in FIG. 5, a first, larger ROI 200 having radius R comprises the entire field of view (FOV), while a second, smaller ROI 202 having radius r is a region encompassing the heart 204 of a patient 22 being scanned. Assumptions used in some configurations of the present invention useful for cardiac imaging are that the projection data acquired from the larger ROI 200 is band-limited to a bandwidth $b_t$ in the temporal frequency domain $u_t$, and the projection data acquired from the smaller ROI 202 is bandlimited to a bandwidth $B_t$ in the temporal frequency domain $u_t$, as illustrated in FIG. 6.

The highest angular frequency in the projection data acquired from a parallel beam x-ray source is a linear function of the radius of the FOV, i.e., $|u_\theta| \leq r u_\rho$ for ROI 202 of radius r, where $u_\rho$ is the support of the spectrum of the projection data acquired from the object. Therefore, the highest angular frequency for the second, smaller ROI 202 is $|u_{\theta 1}| \leq r u_\rho$, and the highest angular frequency for the first, larger ROI 200 is $|u_{\theta 2}| \leq R u_\rho$. Although these results directly relate to data acquisition with a parallel beam x-ray source, the results are equally applicable to other acquisition configurations, e.g., fan-beam acquisition, in which there is a linear relationship between angular bandwidth and projection data bandwidth for a given radius of the ROI.

There should be no aliasing in the $(u_\rho, u_\theta, u_t)$ domain in reconstructions of a fan beam projection data $f(\rho,\theta,t)$ made from its samples. The acquisition along $\rho$ can be assumed to be continuous and reasonably bandlimited, so that 3-D sampling problem can be simplified to 2-D sampling problem. Thus, in some configurations of the present invention, the angular bandwidth for the second, smaller ROI 202 and the first, larger ROI 200 is taken as the maximum bandwidths $B_{\theta 1} = r u_\rho$ and $B_{\theta 2} = R u_\rho$, respectively, so that aliasing in the $(u_\theta, u_t)$ domain is avoided, which also avoids aliasing in $(u_\theta, u_\rho, u_t)$ domain.

Figure 6:
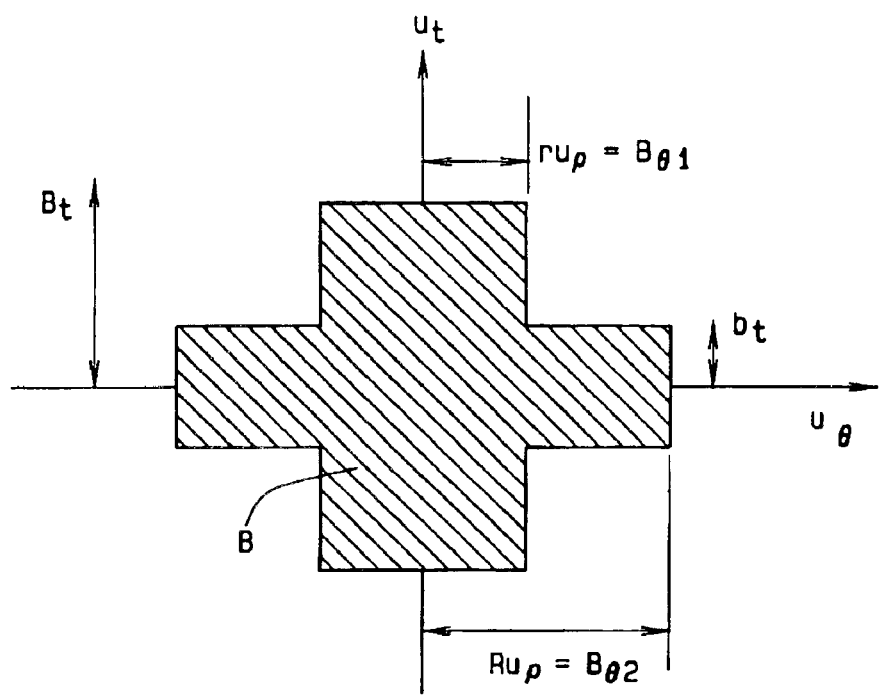
FIG. 6 is a representation of spectral support of a projection data set.

Combining the above assumptions results in the maximum 2-D spectral support for projection $f(\theta, t)$, as illustrated in FIG. 6.

Spatial support S is defined as the sampling range of $\theta$. In configurations utilizing a 360 degree scan, S is $2\pi$. In configurations utilizing a 180 degrees plus fan angle scan, S is 180 degrees plus the fan angle of the x-ray beam. The 2-D spectral support B is as defined in FIG. 6.

A sampling lattice is selected that (1) is time-sequential with respect to spatial support S. i.e., projection data at only one particular view angle position are acquired at one time, and (2) has a spectral representation that packs spectral support B and its replicates at least tightly. In some configurations, the sampling lattice packs spectral support B and its replicates as tightly as possible.

In configurations utilizing a 360 degree scan, the projection $f(\theta,t)$ is periodic in $\theta$ with the period being $2\pi$. Therefore, to make the lattice time-sequential with respect to $2\pi$, a generating lattice of $2\pi$ is selected. In configurations utilizing a 180 degree plus fan angle scan, a generating lattice can be selected within a range from $\pi$+fanangle to $2\pi$, where fanangle represents the fan angle of the x-ray beam. In some configurations, the generating lattice is $\pi$+fanangle, which provides a temporally uniform lattice that tiles spatial support S over real space R. In configurations for which a temporally uniform lattice is desired, the generating lattice should be the same as spatial support S.

Figure 7:
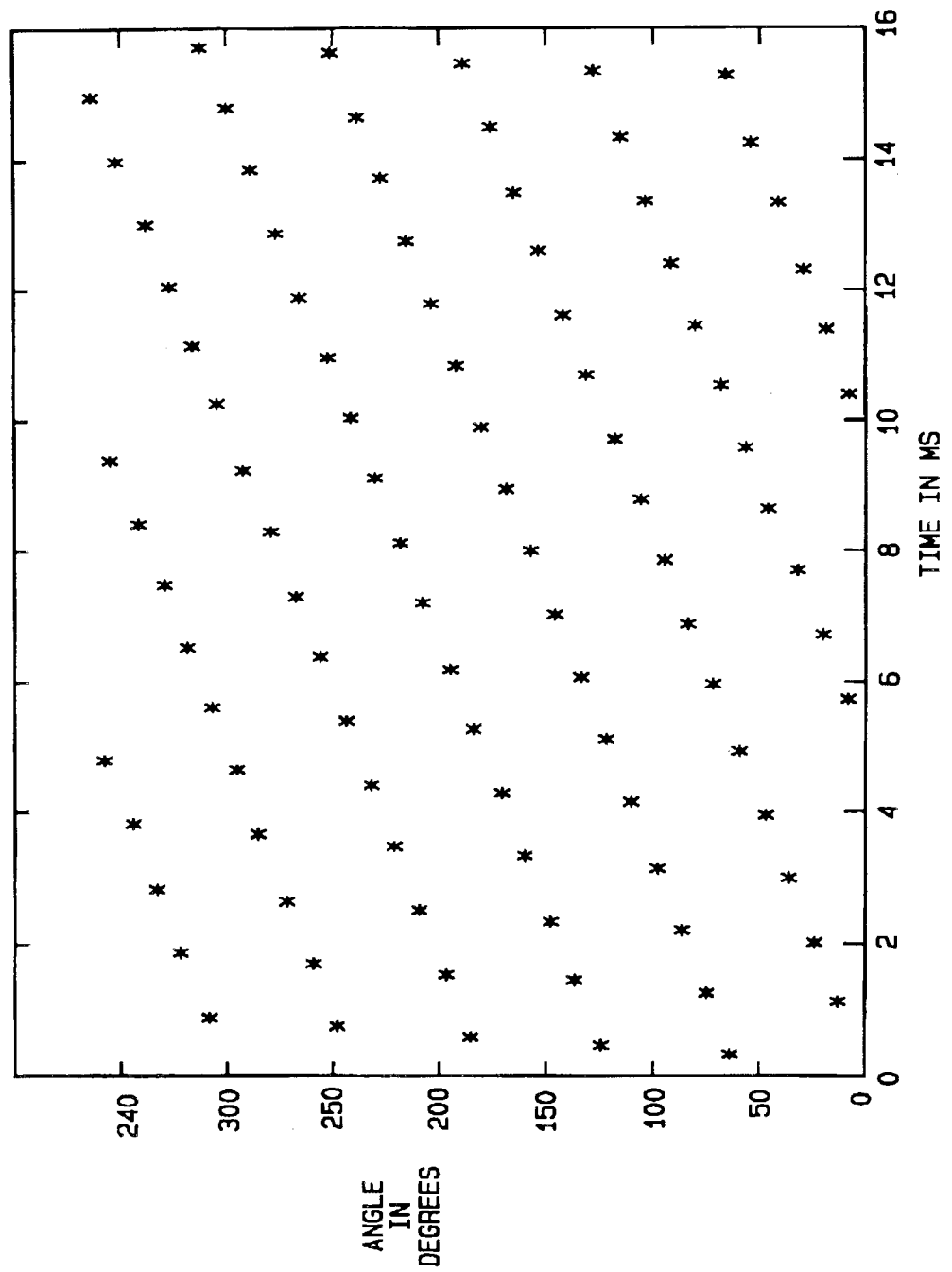
FIG. 7 is an example of an optimal sampling lattice useful in some configurations of the present invention.

An optimal sampling lattice is a lattice that packs B critically, subject to the constraint that its basis A* can be written as:

$$A^* = \begin{bmatrix} \frac{p}{S} & \frac{l}{S} \\ u_1 & u_2 \end{bmatrix} \quad (1)$$

where p and l are coprime integers and $u_1/u_2$ is a rational number. (See Willis and Bresler, "Optimal scan for time-varying tomography II: efficient design and validation," in IEEE Transaction of Image Processing, Vol. 4, No. 5, May 1995.) An example of an optimal sampling lattice useful in some configurations of the present invention is shown in FIG. 7, where the various points represent times and angles at which projections are acquired. However, the sampling lattice illustrated in FIG. 7 is not necessarily optimal in other configurations, and, in general, optimal sampling lattices must be determined for each configuration.

To determine an optimal sampling lattice in configurations in which the number of views K is not limited, a lattice $\Lambda_{critical}$ is determined that packs B critically. A polar lattice is found that is close to $\Lambda_{critical}$, packs B and satisfies constraint (1). The sampling lattice has basis A, which is obtained from the equation $A=(A^*)^{-T}$.

The temporal interval between two successive samples is $T_r=1/(p \cdot u_2 - l \cdot u_1)$. The number of views $K=p \cdot v_2 - l \cdot v_1$, where $v_1/v_2$ $u_1/u_2$, and $v_1, v_2$ are coprime (i.e., relatively prime) integers.

For example, for the spectral support described above, one choice of critical packing lattice whose basis is written:

$$\Lambda^*_{critical} = \begin{bmatrix} 4B_{\theta 1} & 2B_{\theta 1} \\ 2b_t & B_t + 3b_t \end{bmatrix}.$$

Figure 8:
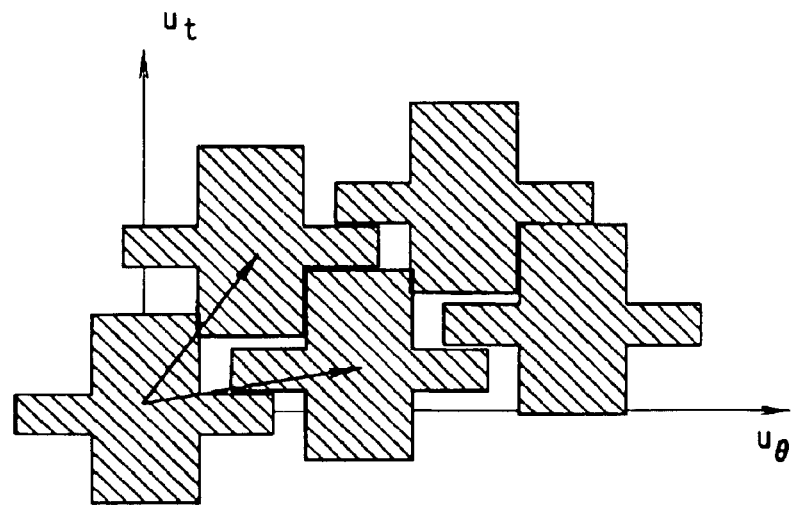
FIG. 8 is a representation of the packing of the spectral support of the projection data in the frequency domain of the sampled signal in some configurations of the present invention.

The packing of spectral support B is shown in FIG. 8. The smallest p and l are selected that satisfy $$\frac{p}{S} = 4B_{\theta 1} + \Delta 1, \frac{l}{S} = 2B_{\theta 1} + \Delta 2,$$

and $\Delta 1 \geq \Delta 2$, where p and l are coprime integers. For the "cross shaped" spectral support B illustrated in FIG. 8, this assures $\Lambda^*$ still packs B.

In configurations in which the number of views K is fixed, a polar lattice $\Lambda^*$ is found that has basis [K/S]. An optimal sampling lattice in such configurations is a lattice having a polar lattice that packs B critically, subject to the constraint that its basis A* can be written as:

$$A^* = \begin{bmatrix} \frac{K}{S} & \frac{l}{S} \\ 0 & u \end{bmatrix}. \quad (2)$$

where l and K are coprime integers, and u is a real number. The temporal interval between two successive samples is $T=1/(uK)$.

The optimal sampling lattice can be determined by selecting an upper triangular polar lattice $\Lambda^*$ that packs B. A polar lattice is selected that is close to $\Lambda^*$, packs B and satisfies constraint (2). The optimal sampling basis is obtained from $A=(A^*)^{-T}$.

For example, for the spectral support B illustrated in FIG. 6, one choice of basis for an upper triangular polar packing lattice is $$A^* = \begin{bmatrix} \frac{K}{S} & B_{\theta 1} + B_{\theta 2} \\ 0 & u \end{bmatrix}.$$

Figure 9:
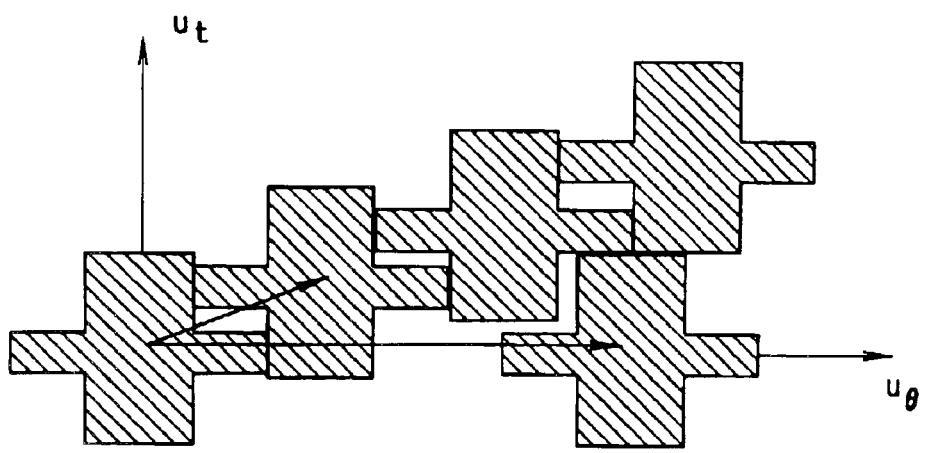
FIG. 9 is a representation of the packing of the spectral support of the projection data in the frequency domain of the sampled signal in some other configurations of the present invention.

This packing of spectral support B is illustrated in FIG. 9. If $m=[B_{\theta 1}S]$ is the smallest integer that is larger than $B_{\theta 1}S$, $n=[B_{\theta 2}S]$ and g is the improvement factor over linear sampling that is desired for a particular configuration, then $u=2B_t/g$. The value of g can be fixed, in which case the smallest number of views K needed can be determined, or the value of K can be fixed, in which case the smallest value for u can be determined, i.e., the largest improvement factor g.

In some configurations in which g is fixed, the following conditions are satisfied to avoiding overlapping $K>=(g-1)*(m+n)+2*n$     (a)

$(g-1)u>B_t+b_t$.     (b)

In some configurations, a value of K is chosen that is the smallest integer that satisfies condition (a) and is coprime with m+n. Then the basis of the polar lattice can be written as $$A^* = \begin{bmatrix} \frac{K}{S} & \frac{m}{S} + \frac{n}{S} \\ 0 & \frac{2B_t}{g} \end{bmatrix}.$$

Condition (b) assures that the polar basis A* above allows the largest $b_t=B_t*(g-2)/g$ without overlapping.

In configurations in which K is limited, from the above polar basis A*, the optimal sampling basis A in an upper triangular form is written:

$$A = \begin{bmatrix} \frac{S}{K} & 0 \\ a_{21} & \frac{g}{2B_t} \end{bmatrix}.$$

The sampling pattern $\{t_n, \theta_n\}$ or lattice can be derived from the sampling basis.

Reconstruction can be achieved by 2-D linear filtering followed by standard fan beam filtered backprojection methods. To perform reconstruction in some configurations of the present invention, samples on the lattice $\{t_n,\theta_n\}$ are interpolated to samples on rectangular grid $\{nT,n\Delta\theta\}$. Here, $$T = \frac{g}{2B_t K}, \text{ and } \Delta\theta = \frac{S}{K}.$$

Figure 10:
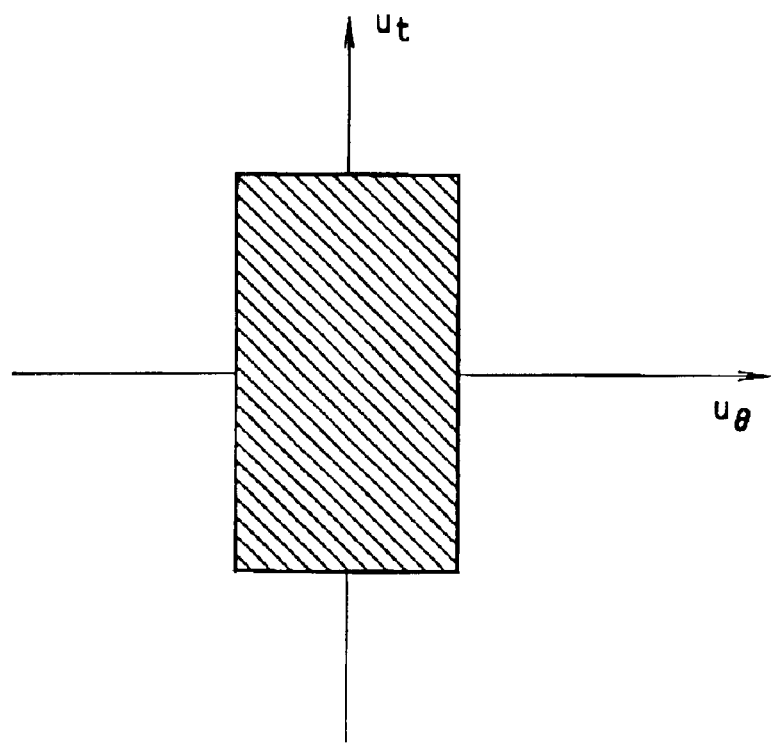
FIG. 10 is a representation of the ideal frequency response of one of two filters that are used to filter the sampled projection data.
Figure 11:
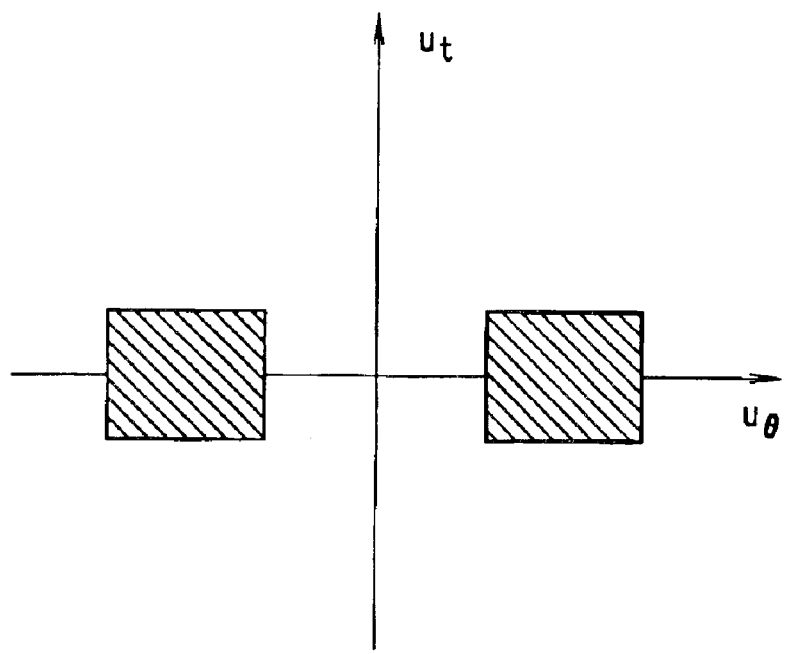
FIG. 11 is a representation of the ideal frequency response of a second of two filters that are used to filter the sampled projection data.

The interpolation is implemented by 2-D filtering. The ideal frequency response of the filter has value 1.0 inside the spectral support B and value 0.0 outside the spectral support B. This filter can be decomposed to two separable, non-overlapping filters as illustrated in FIG. 10 and FIG. 11. The interpolated signal is the sum of the outputs from these two filters.

In some configurations, each 2-D filter is implemented as a cascade of two 1-D filters. Filtering in time direction is applied first and filtering in the angular direction is applied next. The finite impulse response temporal filter is designed using a least square criterion, and is applied to the signal using direct convolution. Since the signal is $2\pi$ periodic in the angular direction, the angular filtering is implemented using the Discrete Fourier Transform (DFT) directly. The filtering is applied in some configurations to each ray in the $\rho$ direction.

Figure 12:
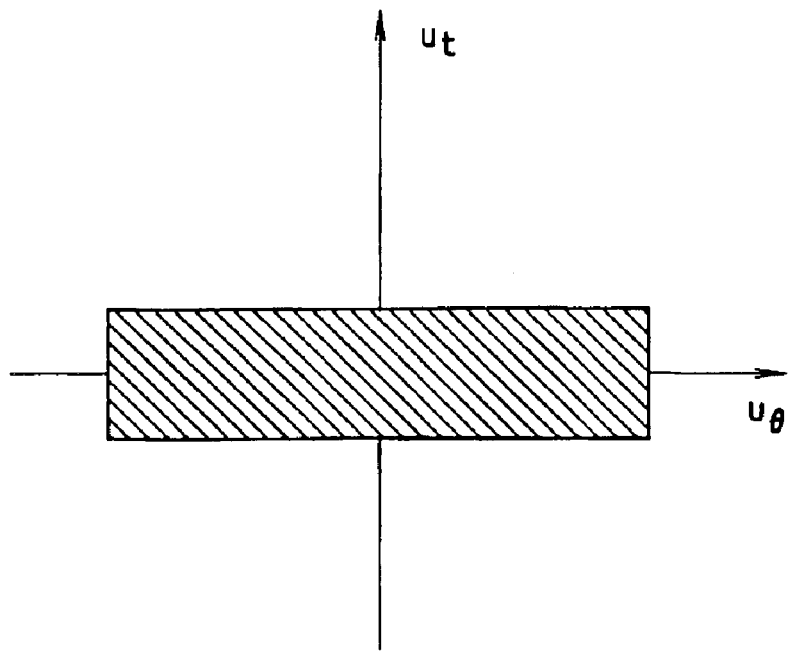
FIG. 12 is an alternative to the ideal filter of FIG. 11 that is used in some configurations of the present invention.

To the extent that the assumption of the spectral support B is correct, then for any ray inside the smaller ROI 202 in FIG. 5, $f(\rho_0,\theta_n,t_n)$ can be filtered approximately using the filter illustrated in FIG. 10. For any ray outside the small ROI 202 in FIG. 5, $f(\rho_0,\theta_n,t_n)$ is filtered using the filter illustrated in FIG. 12.

After the interpolation, the image is reconstructed using any suitable known method.

In one example configuration, the parameters for the optimal sampling lattice design are chosen as the following:
$B_t=10.0$ Hz, $b_t=6.0$ Hz, $r=12.0$ cm, $R=22.0$ cm, u_theta1= 30, u_theta2=55, g=3.

The designed optimal sampling basis is:

$$A = \begin{bmatrix} 0.0043 & 0 \\ -0.0554 & 0.150 \end{bmatrix}$$

The number of views is K=943, the temporal interval between two successive views is about $T_r=159$ ns, the sweep time is $KT_r=150$ ms. Since it is assumed that the temporal bandwidth is $B_t=10$ Hz, a temporal resolution of 50 ms is obtained with a 150 ms sweep time, achieving a factor of 3 improvement over the linear sampling lattice. Projection data were simulated using a dynamic heart model, assuming the heart rate is fixed at 60 Hz. By increasing $B_t$ to 20.0 Hz and keeping all other parameters unchanged, the optimal sampling basis is obtained:

$$A = \begin{bmatrix} 0.0043 & 0 \\ -0.0227 & 0.075 \end{bmatrix}$$

The number of views is K=943, the temporal interval between two successive views is about $T_r=79.5$ ns, and the sweep time is $KT_r=75$ ms. Thirty-two sweeps are collected, so the total data collection time is 32*0.075=2.4 seconds. In the reconstruction, the filter length is chosen to be 22.

In configurations in which there are multiple sources 14 in FIG. 2, for example, N sources 14, turned on at the same time and they are separated by 360/N degree, the sampling range of $\theta$ for each source is 360/N. The sampling pattern for each source within the range 360/N is still subject to the time-sequential constraint, and can be designed in a manner similar to that described above. For example, the predetermined sampling lattice is a sampling lattice that is time-sequential with respect to spatial support S defined as a sampling range of view angles $\theta$ and optimally (or at least tightly) packs spectral support B.

Some configurations of the present invention relax the temporal sampling requirements by a factor of between 3 and 4. For example, to obtain temporal resolution of 50 ms, a scan is completed at an interval of 150 ms or 200 ms, while still preserving image quality. This relaxation of the temporal sampling requirement also relaxes hardware requirements greatly. Since it is possible to scan relatively slowly, more X-ray flux can be produced, and in turn, higher signal-to-noise ratio (SNR) and better image quality can be obtained. Because various configurations of the present invention do not rely on periodicity of heart motion, image reconstruction is robust with respect to heart rate variations.

Figure 13:
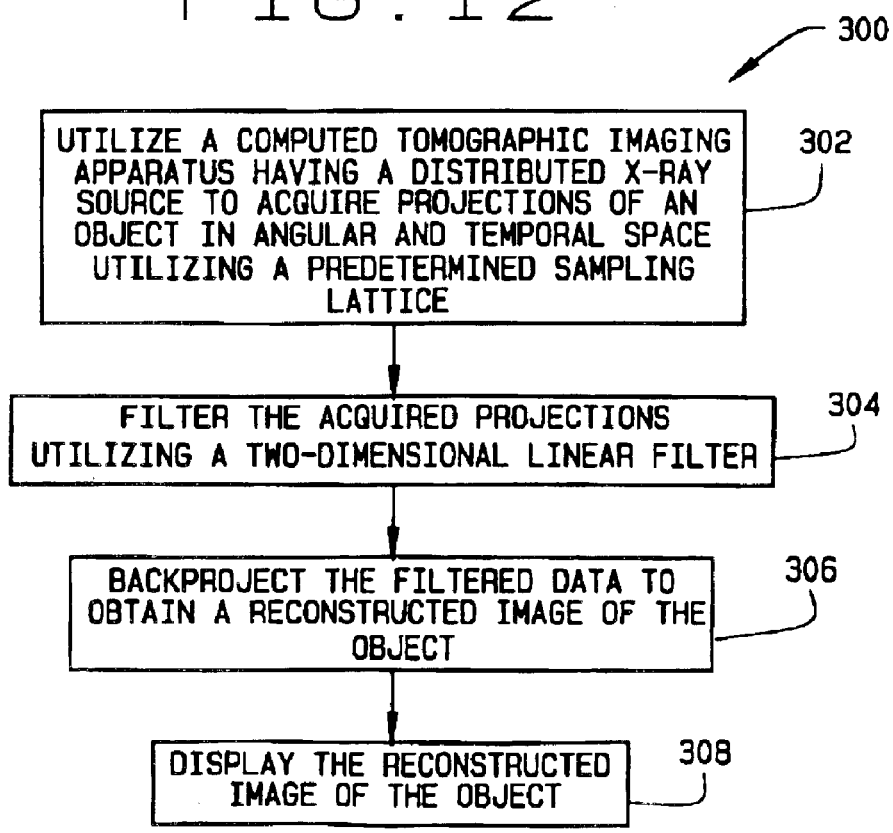
FIG. 13 is a flow chart representative of some configurations of the present invention.

More particularly, and referring to flowchart 300 of FIG. 13, a technical effect of CT imaging apparatus 10 having distributed x-ray sources is achieved by a user first utilizing the imaging apparatus to acquire samples of projection data of an object in angular and temporal space utilizing a predetermined sampling lattice, as at 302. In some configurations, the predetermined sampling lattice is a sampling lattice that is time-sequential with respect to spatial support S defined as a sampling range of angles $\theta$ and that at least tightly packs spectral support B. The acquired projections are filtered at 304 utilizing a two-dimensional linear filter. In some configurations, the two-dimensional linear filter has a constant frequency response (e.g., 1.0) inside a predefined spectral support, and a zero (0.0) frequency response elsewhere. Also in some configurations, the filtering of the acquired projections comprises filtering in a temporal direction utilizing a finite impulse response filter and filtering in an angular direction utilizing a direct Discrete Fourier Transform. The filtered projections are then backprojected at 306 to obtain a reconstructed image of the object. The reconstructed image can then be displayed at 308, for example, utilizing display 42 shown in FIG. 2.

Also, in some configurations of the present invention, a complete scan is made at intervals between about 150 ms and about 200 ms. The object being imaged may be a heart of a medical patient or another object that is at least partially in motion, although configurations of the present invention are not limited to imaging moving objects.

Thus, it will be appreciated that methods and apparatus of the present invention suppress motion artifacts effectively while maintaining a high signal-to-noise ratio in images of a moving object. Moreover, methods and apparatus of the present invention are particularly useful for cardiac CT imaging, inasmuch as the suppression of motion artifacts does not depend upon the periodicity and regularity of the motion of the heart.

While the invention has been described in terms of various specific embodiments, those skilled in the art will recognize that the invention can be practiced with modification within the spirit and scope of the claims.

What is claimed is:

1. A method for imaging an object comprising:
   utilizing a computed tomographic imaging apparatus having a distributed x-ray source to acquire samples of projection data of an object in angular and temporal space utilizing a predetermined sampling lattice;
   filtering acquired projection data utilizing a two-dimensional linear filter to thereby produce filtered data; and backprojecting the filtered data to obtain a reconstructed image of the object.

2. A method in accordance with claim 1 wherein the two-dimensional linear filter has a constant frequency response inside a predefined spectral support and zero frequency response elsewhere.

3. A method for imaging an object comprising:
utilizing a computed tomographic imaging apparatus having a distributed x-ray source to acquire samples of projection data of an object in angular and temporal space utilizing a predetermined sampling lattice, wherein the predetermined sampling lattice is a sampling lattice that is time-sequential with respect to spatial support S defined as a sampling range of view angles $\theta$ and that at least tightly packs spectral support B of the object in the frequency domain;
filtering acquired projection data utilizing a two-dimensional linear filter to thereby produce filtered data; and
backprojecting the filtered data to obtain a reconstructed image of the object.

4. A method in accordance with claim 3 wherein the two-dimensional linear filter has a constant frequency response inside a predefined spectral support and zero frequency response elsewhere.

5. A method in accordance with claim 3 wherein said filtering acquired projection data comprises filtering in a temporal direction utilizing a finite impulse response (FIR) filter and filtering in an angular direction utilizing a direct Discrete Fourier Transform (DFT).

6. A method in accordance with claim 3 wherein the distributed x-ray source comprises a plurality of x-ray sources.

7. A method in accordance with claim 3 wherein a complete scan is made at intervals of between about 150 ms and 200 ms.

8. A method in accordance with claim 3 wherein the object being imaged includes a heart of a medical patient.

9. A method in accordance with claim 3 wherein the object being imaged is at least partially in motion.

10. A method in accordance with claim 3 further comprising displaying the reconstructed image of the object.

11. A computed tomographic imaging apparatus comprising:
a distributed x-ray source and a detector configured to acquire samples of projection data of an object in angular and temporal space utilizing a predetermined sampling lattice,
said apparatus configured to:
filter acquired projection data utilizing a two-dimensional linear filter to thereby produce filtered data; and
backproject the filtered data to obtain a reconstructed image of the object.

12. An apparatus in accordance with claim 11 wherein the two-dimensional linear filter has a constant frequency response inside a predefined spectral support and zero frequency response elsewhere.

13. An apparatus in accordance with claim 11 configured to perform a complete scan at intervals of between about 150 ms and 200 ms.

14. An apparatus in accordance with claim 11 further comprising a display configured to display the reconstructed image of the object.

15. A computed tomographic imaging apparatus comprising:
a distributed x-ray source and a detector configured to acquire samples of projection data of an object in angular and temporal space utilizing a predetermined sampling lattice, wherein the predetermined sampling lattice is a sampling lattice that is time-sequential with respect to spatial support S defined as a sampling range of view angles $\theta$ and that at least tightly packs spectral support B of the object in the frequency domain;
said apparatus configured to:
filter acquired projection data utilizing a two-dimensional linear filter to thereby produce filtered data; and
backproject the filtered data to obtain a reconstructed image of the object.

16. An apparatus in accordance with claim 15 wherein the two-dimensional linear filter has a constant frequency response inside a predefined spectral support and zero frequency response elsewhere.

17. An apparatus in accordance with claim 15 wherein to filter acquired projection data, said apparatus is configured to filter projection data in a temporal direction utilizing a finite impulse response (FIR) filter and to filter projection data in an angular direction utilizing a direct Discrete Fourier Transform (DFT).

18. An apparatus in accordance with claim 17 wherein said distributed x-ray source comprises a plurality of x-ray sources.

19. An apparatus in accordance with claim 15 configured to perform a complete scan at intervals of between about 150 ms and 200 ms.

20. An apparatus in accordance with claim 15 further comprising a display configured to display the reconstructed image of the object.

* * * * *